United States Patent
Flaherty et al.

(10) Patent No.: US 7,128,727 B2
(45) Date of Patent: Oct. 31, 2006

(54) COMPONENTS AND METHODS FOR PATIENT INFUSION DEVICE

(76) Inventors: J. Christopher Flaherty, 242 Ipswich Rd., Topsfield, MA (US) 01983; William Gorman, 62 Lakeshore Dr., South Hamilton, MA (US) 01982; John T. Garibotto, 29 Winthrop St., Charlestown, MA (US) 02129; John R. Bussiere, 9 Gray Farm Rd., Littleton, MA (US) 01460; Matthew D. Abelson, 83A Boston St., Somerville, MA (US) 02143; David P. Chastain, 21 Washington Dr., Acton, MA (US) 01720

( * ) Notice: Subject to any disclaimer, the term of this patent is extended or adjusted under 35 U.S.C. 154(b) by 54 days.

(21) Appl. No.: 10/260,192

(22) Filed: Sep. 30, 2002

(65) Prior Publication Data

US 2004/0064096 A1 Apr. 1, 2004

(51) Int. Cl.
*A61M 37/00* (2006.01)
*A61M 5/178* (2006.01)

(52) U.S. Cl. .................................. 604/131; 604/164.07

(58) Field of Classification Search ................ 604/131, 604/158, 164.01, 164.04, 160, 164.07, 264, 604/167, 184; 606/167, 184, 185
See application file for complete search history.

(56) References Cited

U.S. PATENT DOCUMENTS

| | | | |
|---|---|---|---|
| 3,631,847 A | | 1/1972 | Hobbs |
| 3,792,703 A | * | 2/1974 | Moorehead .................. 604/158 |
| 3,812,843 A | | 5/1974 | Wooten et al. |
| 3,885,662 A | | 5/1975 | Schaefer |
| 4,067,000 A | | 1/1978 | Carlson |
| 4,108,177 A | | 8/1978 | Pistor |
| 4,151,845 A | | 5/1979 | Clemens |
| 4,193,397 A | | 3/1980 | Tucker et al. |
| 4,211,998 A | | 7/1980 | Junginger et al. |
| 4,231,019 A | | 10/1980 | Junginger et al. |
| 4,268,150 A | | 5/1981 | Chen |
| 4,342,311 A | | 8/1982 | Whitney et al. |
| 4,364,385 A | | 12/1982 | Lossef |
| 4,373,527 A | | 2/1983 | Fischell |
| 4,424,720 A | | 1/1984 | Bucchianeri |

(Continued)

FOREIGN PATENT DOCUMENTS

DE 4200595 7/1993

(Continued)

OTHER PUBLICATIONS

Web-Site Brochure dated Jan. 4, 2000. SOOIL-Homepage. "Portable Insulin Pump", www.sooil.com/product2.htm.

(Continued)

*Primary Examiner*—Nicholas D. Lucchesi
*Assistant Examiner*—Matthew F. DeSanto

(57) ABSTRACT

A transcutaneous access tool includes a first cannula moveable along an axis, a fixed member including an elongated prong extending parallel with the axis, and a deployment member secured to the first cannula and movable along the axis away from the fixed member. The deployment member includes spaced-apart, resiliently flexible fingers extending parallel with the axis and having distal ends that are laterally enlarged with respect to the axis. The resiliently flexible fingers are received on the prong of the fixed member. A second cannula is disposed within the lumen of the first cannula, and retraction member is secured to the second cannula and is movable along the axis. The retraction member includes at least one catch catching on the laterally enlarged distal ends of the fingers of the deployment element when the fingers are laterally held apart by the prong of the fixed member.

3 Claims, 8 Drawing Sheets

U.S. PATENT DOCUMENTS

| | | |
|---|---|---|
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopk |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| D303,013 S | 8/1989 | Konopka |
| 4,855,746 A | 8/1989 | Stacy |
| 4,871,351 A | 10/1989 | Feingold |
| 4,882,600 A | 11/1989 | Van de Moere |
| 4,886,499 A | 12/1989 | Cirelli et al. |
| 4,898,578 A | 2/1990 | Rubalcaba, Jr. |
| 4,898,579 A | 2/1990 | Groshong et al. |
| D306,691 S | 3/1990 | Arai |
| 4,944,659 A | 7/1990 | Labbe et al. |
| D311,735 S | 10/1990 | Arai et al. |
| 4,969,874 A | 11/1990 | Michel et al. |
| 4,973,998 A | 11/1990 | Gates |
| D315,727 S | 3/1991 | Arai et al. |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,125,415 A | 6/1992 | Bell |
| 5,176,662 A | 1/1993 | Bartholomew et al. |
| 5,178,609 A | 1/1993 | Ishikawa |
| 5,189,609 A | 2/1993 | Tivig et al. |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,242,406 A | 9/1993 | Gross et al. |
| 5,244,463 A | 9/1993 | Cordner, Jr. et al. |
| 5,245,447 A | 9/1993 | Stemmle |
| 5,254,096 A | 10/1993 | Rondelet et al. |
| 5,257,980 A | 11/1993 | Van Antwerp et al. |
| 5,281,202 A | 1/1994 | Weber et al. |
| 5,308,335 A | 5/1994 | Ross et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A | 9/1994 | Elson |
| 5,364,342 A | 11/1994 | Beuchat et al. |
| 5,411,480 A | 5/1995 | Kriesel |
| 5,433,710 A | 7/1995 | Van Antwerp et al. |
| 5,452,033 A | 9/1995 | Balling et al. |
| 5,492,534 A | 2/1996 | Athayde et al. |
| 5,505,709 A | 4/1996 | Funderburk et al. |
| 5,507,288 A | 4/1996 | Böcker et al. |
| 5,514,096 A | 5/1996 | Hiejima |
| 5,533,389 A | 7/1996 | Kamen et al. |
| 5,545,152 A | 8/1996 | Funderburk et al. |
| 5,573,342 A | 11/1996 | Patalano |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,660,728 A | 8/1997 | Saaski et al. |
| 5,665,065 A | 9/1997 | Colman et al. |
| 5,665,070 A | 9/1997 | McPhee |
| 5,678,539 A | 10/1997 | Schubert et al. |
| 5,685,859 A | 11/1997 | Kornerup |
| 5,695,490 A | 12/1997 | Flaherty et al. |
| 5,702,363 A | 12/1997 | Flaherty |
| 5,704,520 A | 1/1998 | Gross |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,764,159 A | 6/1998 | Neftel |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson |
| 5,800,405 A | 9/1998 | McPhee |
| 5,810,015 A | 9/1998 | Flaherty |
| 5,814,020 A | 9/1998 | Gross |
| 5,839,467 A | 11/1998 | Saaski et al. |
| 5,840,063 A | 11/1998 | Flaherty |
| 5,845,218 A | 12/1998 | Altschul |
| 5,848,991 A | 12/1998 | Gross et al. |
| 5,851,197 A | 12/1998 | Marano et al. |
| 5,858,005 A | 1/1999 | Kriesel |
| 5,858,239 A | 1/1999 | Kenley |
| D405,524 S | 2/1999 | Falk et al. |
| 5,865,806 A * | 2/1999 | Howell ............... 604/164.12 |
| 5,871,470 A * | 2/1999 | McWha ............... 604/158 |
| 5,875,393 A | 2/1999 | Altschul et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,935,099 A | 8/1999 | Peterson et al. |
| 5,954,058 A | 9/1999 | Flaherty |
| 5,957,890 A | 9/1999 | Mann et al. |
| 5,957,895 A | 9/1999 | Sage et al. |
| 5,961,492 A | 10/1999 | Kriesel et al. |
| 5,965,848 A | 10/1999 | Altschul et al. |
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,024,539 A | 2/2000 | Blomquist |
| 6,061,580 A | 5/2000 | Altschul et al. |
| 6,071,292 A | 6/2000 | Makower et al. |
| 6,144,847 A | 11/2000 | Altschul et al. |
| 6,152,898 A | 11/2000 | Olsen |
| 6,174,300 B1 | 1/2001 | Kriesel et al. |
| 6,190,359 B1 | 2/2001 | Heruth |
| 6,206,850 B1 | 3/2001 | O'Neil |
| 6,244,776 B1 | 6/2001 | Wiley |
| 6,363,609 B1 | 4/2002 | Pickren |
| 6,375,638 B1 | 4/2002 | Nason et al. |

| | | | |
|---|---|---|---|
| 6,520,936 B1 | 2/2003 | Mann | |
| 6,527,744 B1 | 3/2003 | Kriesel et al. | |
| 6,572,585 B1 | 6/2003 | Choi | |
| 2004/0068224 A1 | 4/2004 | Couvillion et al. | |

FOREIGN PATENT DOCUMENTS

| | | | |
|---|---|---|---|
| DE | 19920896 | | 9/2000 |
| EP | 0342947 | | 5/1989 |
| EP | 0763369 | | 3/1997 |
| EP | 0867196 | | 3/1998 |
| EP | 0937475 | | 8/1999 |
| GB | 0763369 | * | 3/1997 |
| WO | WO81/01658 | | 6/1981 |
| WO | WO86/06796 | | 11/1986 |
| WO | WO98/00193 | | 1/1998 |
| WO | WO98/01071 | | 1/1998 |
| WO | WO99/10040 | | 3/1999 |
| WO | WO00/19887 | | 9/1999 |
| WO | WO99/62576 | | 9/1999 |
| WO | WO99/56803 | | 11/1999 |
| WO | WO0010628 | | 3/2000 |
| WO | WO00/29047 | | 5/2000 |
| WO | WO00/29049 | | 5/2000 |
| WO | WO00/74752 | | 5/2000 |
| WO | WO00/30705 | | 6/2000 |
| WO | WO00/78210 | | 6/2000 |
| WO | WO00/48112 | | 8/2000 |
| WO | WO00/61215 | | 10/2000 |
| WO | WO01/52727 | | 1/2001 |
| WO | WO01/5663 | | 8/2001 |
| WO | WO01/76684 | | 10/2001 |
| WO | WO02/20073 | | 3/2002 |
| WO | WO02/26282 | | 4/2002 |

OTHER PUBLICATIONS

Web-Site Brochure dated Jan. 4, 2000. SOOIL-Homepage. "Portable Insulin Pump". www.sooil.com/product3.htm.

Web-Site Brochure dated Jan. 4, 2000. SOOIL-Homepage. "Portable Insulin Pump". www.sooil.com/product4.htm.

Web-Site Brochure dated Dec. 20, 1999. "The Animas R-1000 Insulin Pump". www.animascorp.com/pump_f_s.html.

Web-Site Brochure dated Dec. 20, 1999. "The Animas R-1000 Insulin Pump". www.animascorp.com/pump_f_f.html.

Web-Site Brochure dated Jan. 4, 2000. "Portable Insulin Pump". www.sooil.com/intro2.htm.

Web-Site Brochure dated Jan. 4, 2000. MiniMed 508. "Doing its job. Naturally." www.minimed.com/tiles/mm_113.htm.

Web-Site Brochure dated Dec. 20, 1999. Applied Medical Technology. "508 Pump Information". www.applied-medical.co.uk/508.htm.

Web-Site Brochure dated Jan. 4, 2000. "The Glucose Sensor". www.animascorp.com/sensor_f.html.

US 5,954,699, 09/1999, Jost et al. (withdrawn)

* cited by examiner

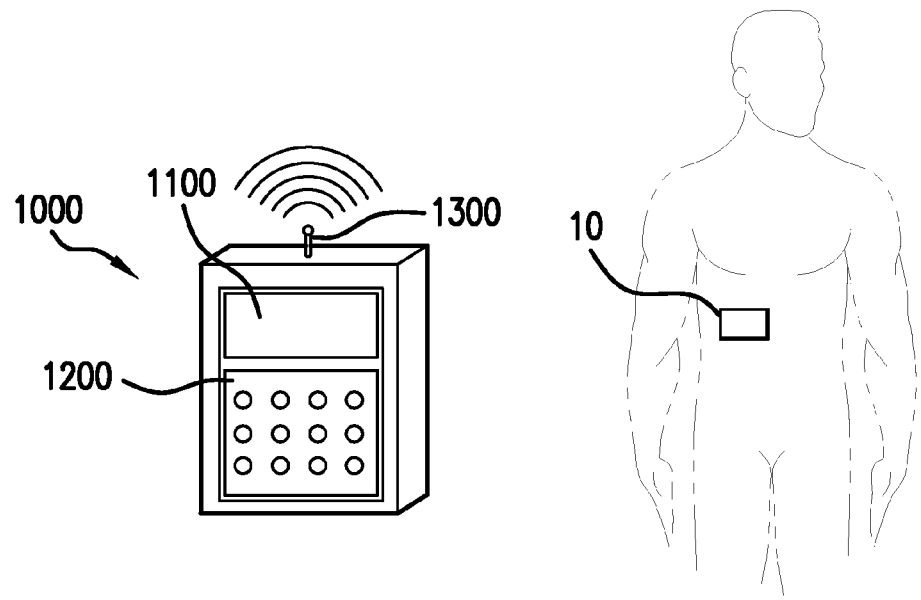
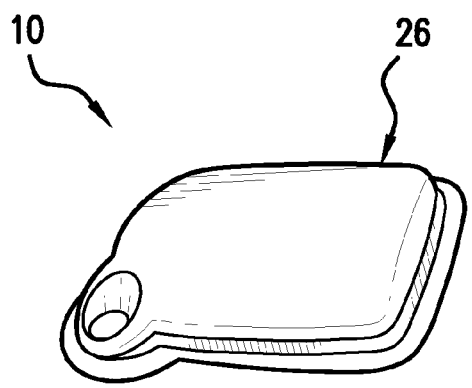
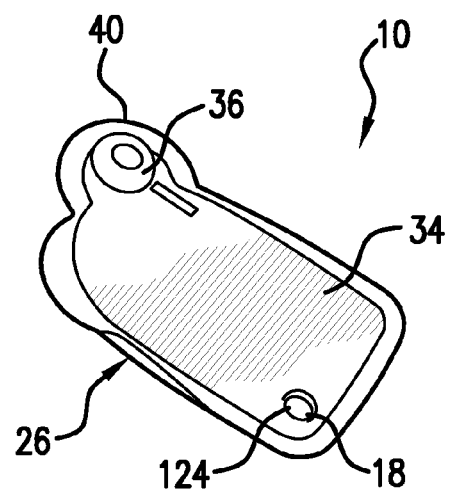

COMPONENTS AND METHODS FOR PATIENT INFUSION DEVICE

CROSS-REFERENCE TO RELATED APPLICATIONS

The present application is related to co-pending U.S. patent application Ser. No. 09/943,992, filed on Aug. 31, 2001, and entitled DEVICES, SYSTEMS AND METHODS FOR PATIENT INFUSION, which is assigned to the assignee of the present application and incorporated herein by reference.

FIELD OF THE INVENTION

The present invention relates generally to medical devices, systems and methods, and more particularly to small, low cost, portable infusion devices and methods that are useable to achieve precise, sophisticated, and programmable flow patterns for the delivery of therapeutic liquids such as insulin to a mammalian patient. Even more particularly, the present invention is directed to various new and improved components and methods for an infusion device.

BACKGROUND OF THE INVENTION

Today, there are numerous diseases and other physical ailments that are treated by various medicines including pharmaceuticals, nutritional formulas, biologically derived or active agents, hormonal and gene based material and other substances in both solid or liquid form. In the delivery of these medicines, it is often desirable to bypass the digestive system of a mammalian patient to avoid degradation of the active ingredients caused by the catalytic enzymes in the digestive tract and liver. Delivery of a medicine other than by way of the intestines is known as parenteral delivery. Parenteral delivery of various drugs in liquid form is often desired to enhance the effect of the substance being delivered, insuring that the unaltered medicine reaches its intended site at a significant concentration. Also, undesired side effects associated with other routes of delivery, such as systemic toxicity, can potentially be avoided.

Often, a medicine may only be available in a liquid form, or the liquid version may have desirable characteristics that cannot be achieved with solid or pill form. Delivery of liquid medicines may best be accomplished by infusing directly into the cardiovascular system via veins or arteries, into the subcutaneous tissue or directly into organs, tumors, cavities, bones or other site specific locations within the body.

Parenteral delivery of liquid medicines into the body is often accomplished by administering bolus injections using a needle and reservoir, or continuously by gravity driven dispensers or transdermal patch technologies. Bolus injections often imperfectly match the clinical needs of the patient, and usually require larger individual doses than are desired at the specific time they are given. Continuous delivery of medicine through gravity feed systems compromise the patient's mobility and lifestyle, and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. An example of a use of an ambulatory infusion pump is for the delivery of insulin for the treatment of diabetes mellitus. These pumps can deliver insulin on a continuous basal basis as well as a bolus basis as is disclosed in U.S. Pat. No. 4,498,843 to Schneider et al.

The ambulatory pumps often work with a reservoir to contain the liquid medicine, such as a cartridge, a syringe or an IV bag, and use electro-mechanical pumping or metering technology to deliver the medication to the patient via tubing from the infusion device to a needle that is inserted transcutaneously, or through the skin of the patient. The devices allow control and programming via electromechanical buttons or switches located on the housing of the device, and accessed by the patient or clinician. The devices include visual feedback via text or graphic screens, such as liquid crystal displays known as LCD's, and may include alert or warning lights and audio or vibration signals and alarms. The device can be worn in a harness or pocket or strapped to the body of the patient.

Currently available ambulatory infusion devices are expensive, difficult to program and prepare for infusion, and tend to be bulky, heavy and very fragile. Filling these devices can be difficult and require the patient to carry both the intended medication as well as filling accessories. The devices require specialized care, maintenance, and cleaning to assure proper functionality and safety for their intended long term use. Due to the high cost of existing devices, healthcare providers limit the patient populations approved to use the devices and therapies for which the devices can be used.

Clearly, therefore, there was a need for a programmable and adjustable infusion system that is precise and reliable and can offer clinicians and patients a small, low cost, lightweight, easy-to-use alternative for parenteral delivery of liquid medicines.

In response, the applicant of the present application provided a small, low cost, light-weight, easy-to-use device for delivering liquid medicines to a patient. The device, which is described in detail in co-pending U.S. application Ser. No. 09/943,992, filed on Aug. 31, 2001, includes an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. To reduce the size, complexity and costs of the device, the device is provided with a housing that is free of user input components, such as a keypad, for providing flow instructions to the local processor. What is still desired, however, are additional new and improved components and methods for devices for delivering fluid to a patient.

SUMMARY OF THE INVENTION

The present invention provides a transcutaneous access tool for use as part of device for delivering fluid, such as insulin for example, to a patient. The transcutaneous access tool includes a first cannula moveable along an axis of the transcutaneous access tool, a fixed member including an elongated prong extending parallel with the axis, and a deployment member secured to the first cannula. The deployment member is movable along the axis away from the fixed member and includes spaced-apart, resiliently flexible fingers extending parallel with the axis and slidingly received on the prong of the fixed member. The fingers having distal ends that are laterally enlarged with respect to the axis.

The transcutaneous access tool also includes a second cannula disposed within the lumen of the first cannula, and a retraction member secured to the second cannula and movable along the axis between the fixed member and the deployment member. The retraction member includes at least one catch extending laterally inwardly with respect to the axis. The catch catches on the laterally enlarged distal ends of the fingers of the deployment element, and prevents the retraction member from being moved away from the deployment member, when the fingers are laterally held apart by the prong of the fixed member.

According to one aspect of the present invention, the transcutaneous access tool further includes a deployment spring biasing the deployment member away from the fixed member, and a retraction spring biasing the retraction member away from the deployment member and towards the fixed member. According to another aspect, the first cannula is flexible and the second cannula is rigid.

The present invention also provides a fluid delivery device including a housing, a reservoir positioned within the housing, and a transcutaneous access tool positioned within the housing. The transcutaneous access tool includes a cannula in fluid communication with the reservoir and linearly moveable along an axis of the transcutaneous access tool through a port in a wall of the housing, a deployment member secured to the cannula and movable along the axis of the transcutaneous access tool against the wall of the housing defining the port, and an annular seal coaxially positioned about the cannula and positioned between the deployment member and the wall of the housing defining the port, so that the seal provides a substantially fluid-tight seal between the deployment member and the wall of the housing when the deployment member is moved against the wall of the housing. The seal allows a fluid or gas, such as a sterilization medium, to enter the exit port from outside the housing prior to deployment of the cannula, but seals the housing in a fluid-tight manner upon deployment of the cannula.

According to one aspect of the present invention, the device also includes an outlet plug removably connected to a distal end of the cannula extending out of the housing, and the port in the wall of the housing comprises an internal exit port and the housing further includes an external exit port for the flexible cannula and a sterilization access port adjacent the external exit port.

The present invention additionally provides a fluid delivery device including a housing having a port providing communication with an interior of the device, an adhesive layer provided on an exterior surface of the housing surrounding the port of the housing and including resilient flaps normally sealing the port in a substantially fluid-tight manner, and a protective layer removably covering the adhesive layer and including a sterilization access tube extending through the flaps of the adhesive layer and into the housing. The sterilization access tube allows a fluid or gas, such as a sterilization medium, to enter the port from outside the housing prior to removal of the protective layer, and the flaps seal the port in a fluid-tight manner after removal of the protective layer.

The present invention also provides a flow path assembly including a base layer having opposing first and second surfaces. The base layer defines a fill chamber outlet port extending through the base layer and between the opposing first and second surfaces, an auxiliary chamber inlet port extending through the base layer and between the opposing first and second surfaces, and a first groove on the second surface of the base layer connecting the fill chamber outlet port to the auxiliary chamber inlet port. The base layer also defines an auxiliary chamber outlet port extending through the base layer and between the opposing first and second surfaces, a reservoir inlet port extending through the base layer and between the opposing first and second surfaces, and a second groove on the second surface of the base layer connecting the auxiliary chamber outlet port to the reservoir inlet port. The base layer further defines a reservoir outlet port extending through the base layer and between the opposing first and second surfaces, a cannula inlet port extending through the base layer and between the opposing first and second surfaces, and a third groove on the second surface of the base layer connecting the reservoir outlet port to the cannula inlet port. The flow path assembly also includes a cover layer substantially covering the second surface of the base layer in a substantially fluid-tight manner.

According to one aspect of the present invention, the base layer is relatively rigid and the cover layer is relatively flexible. According to another aspect, the flow path assembly includes a cannula connector member secured to the first surface of the base layer in a substantially fluid-tight manner and defining a cannula connector chamber in fluid communication with the cannula inlet port of the base layer. According to an additional aspect, the flow path assembly includes a fill port member secured to the first surface of the base layer in a substantially fluid-tight manner and defining a fill port chamber in fluid communication with the fill chamber outlet port of the base layer.

According to another aspect of the present invention, the first surface of the base layer defines an auxiliary recess connecting the auxiliary chamber inlet port and the auxiliary chamber outlet port. According to a further aspect, the assembly includes a sensor assembly secured to the auxiliary chamber recess of the first surface of the base layer in a substantially fluid-tight manner, and the sensor assembly has a sensor chamber in fluid communication with the auxiliary chamber inlet port and the auxiliary chamber outlet port of the base layer.

According to an additional aspect, the first surface of the base layer defines a reservoir shelf connecting the reservoir inlet port and the reservoir outlet port. According to another aspect, the assembly further includes a reservoir secured to the reservoir shelf of the first surface of the base layer in a substantially fluid-tight manner and the reservoir has a reservoir chamber in fluid communication with the reservoir inlet port and the reservoir outlet port. According to yet another aspect, the reservoir includes an end cap closing the open first end of cylindrical side wall in a substantially fluid-tight manner and defining a reservoir port providing fluid communication between the reservoir chamber and the reservoir inlet port and the reservoir outlet port.

The present invention provides another flow path assembly including a cylindrical side wall having opposing first and second open ends and defining a reservoir chamber, an end cap closing the second open end of the side wall and defining a port providing fluid communication with the reservoir chamber, a plunger received in the reservoir chamber and slidingly moveable along the side wall and between the opposing first and second open ends, and a lead screw extending into the first open end of the side wall and having a distal end secured to the plunger.

According to one aspect of the present invention, the flow path assembly further includes a base layer having opposing first and second surfaces, a fill chamber outlet port extending through the base layer and between the opposing first and second surfaces, a reservoir inlet port extending through the base layer and between the opposing first and second surfaces, a reservoir outlet port extending through the base layer and between the opposing first and second surfaces, and a cannula inlet port extending through the base layer and between the opposing first and second surfaces. The second surface of the base layer defines a first groove connecting the fill chamber outlet port to the reservoir inlet port, and a second groove connecting the reservoir outlet port to the cannula inlet port. The first surface of the base layer defines a reservoir recess connecting the reservoir inlet port and the reservoir outlet port and receiving the end cap of the reservoir in a substantially fluid-tight manner. The port of the end cap provides fluid communication between the reservoir chamber and the reservoir inlet port and the reservoir outlet port.

The present invention provides an additional flow path assembly including a first portion and a second portion of a housing of a fluid delivery device assembled together to form an end wall of the housing. The end wall includes a fill port, a reservoir connection port, a cannula connection port, and at least one flow path connecting the fill port, the reservoir connection port and the cannula connection port.

According to one aspect of the present invention, the first portion of the housing includes a first portion of the end wall and the second portion of the housing includes a second portion of the end wall. The first and the second portions of the end wall have mating surfaces defining corresponding grooves which together define the flow path of the end wall when the first and the second portions of the housing are assembled together.

These aspects of the invention together with additional features and advantages thereof may best be understood by reference to the following detailed descriptions and examples taken in connection with the accompanying illustrated drawings.

BRIEF DESCRIPTION OF THE DRAWINGS

FIG. 1 is a perspective view of a first exemplary embodiment of a fluid delivery device constructed in accordance with the present invention shown secured on a patient, and a remote control device for use with the fluid delivery device (the remote control device being enlarged with respect to the patient and the fluid delivery device for purposes of illustration);

FIGS. 2a and 2b are enlarged top and bottom perspective views, respectively, of the fluid delivery device of FIG. 1;

Like reference characters designate identical or corresponding components and units throughout the several views.

DETAILED DESCRIPTION OF THE EXEMPLARY EMBODIMENTS

Figure 3:
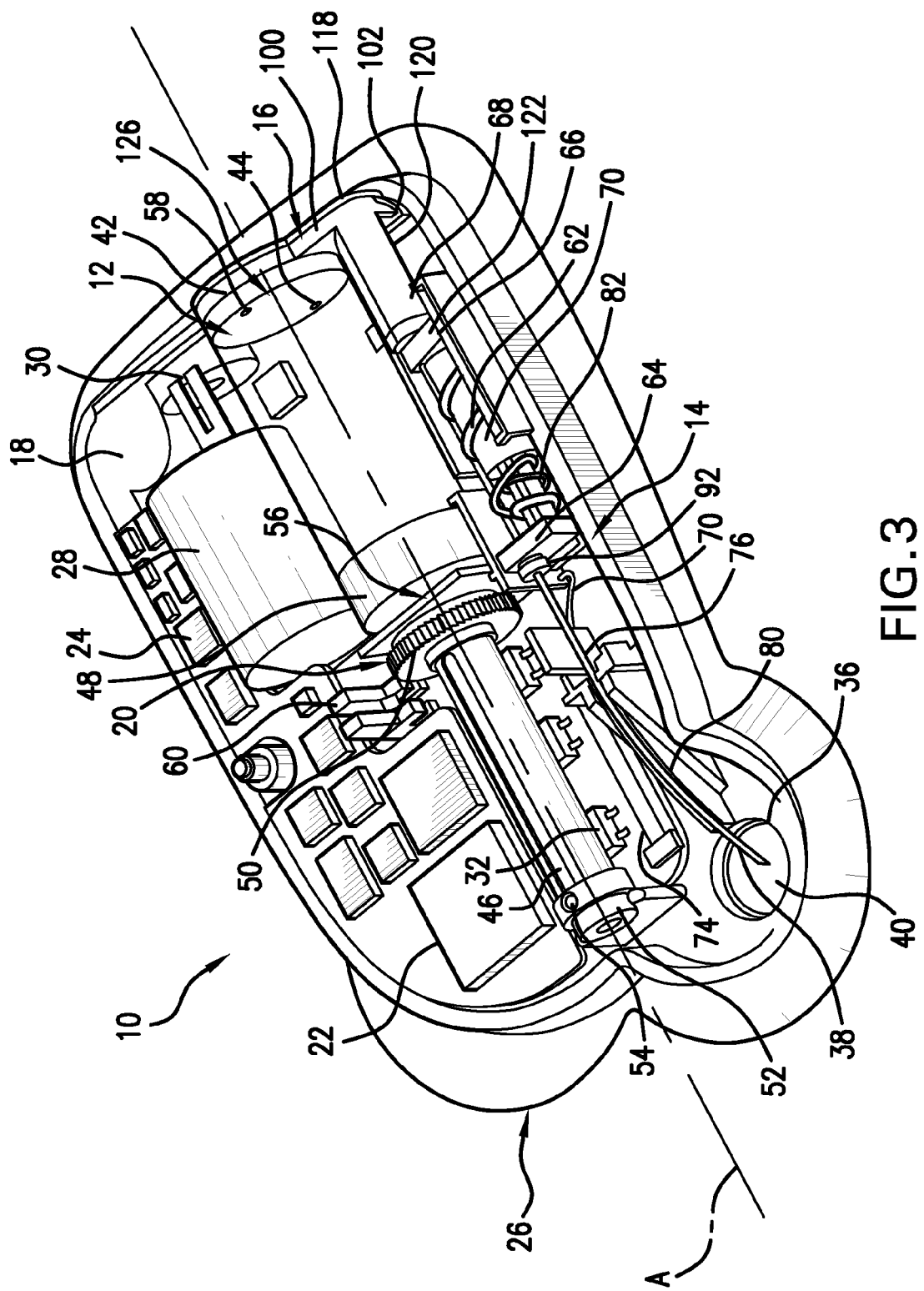
FIG. 3 is a further enlarged top perspective view of the fluid delivery device of FIG. 1, shown with a top housing portion removed to reveal interior portions of the fluid delivery device, including an exemplary embodiment of a transcutaneous access tool constructed in accordance with the present invention and an exemplary embodiment of a laminated flow path constructed in accordance with the present invention.

Referring to FIGS. 1 through 3, there is illustrated an exemplary embodiment of a fluid delivery device 10 constructed in accordance with the present inventions. Referring to FIG. 3, the fluid delivery device 10 includes exemplary embodiments of a reservoir 12 for receiving and holding fluid to be delivered by the device 10, a transcutaneous access tool 14 for providing fluid communication between the reservoir 12 and a patient, and a laminated flow path assembly 16 connecting a fill port 18 to the reservoir 12 and the reservoir to the transcutaneous access tool 14, all constructed in accordance with the present inventions.

The fluid delivery device 10 can be used for the delivery of fluids to a person or animal. The types of liquids that can be delivered by the fluid delivery device 10 include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery device 10 might be used to treat include, but are not limited to, diabetes, cardiovascular disease, pain, chronic pain, cancer, AIDS, neurological diseases, Alzheimer's Disease, ALS, Hepatitis, Parkinson's Disease or spasticity. The volume of the reservoir 12 is chosen to best suit the therapeutic application of the fluid delivery device 10 impacted by such factors as available concentrations of medicinal fluids to be delivered, acceptable times between refills or disposal of the fluid delivery device 10, size constraints and other factors.

The fluid delivery device 10 also includes a dispenser 20 for causing fluid from the reservoir 12 to flow to the transcutaneous access tool 14. A processor or electronic microcontroller (hereinafter referred to as the "local" processor) 22 is connected to the dispenser 20, and is programmed to cause a flow of fluid to the transcutaneous access tool 14 based on flow instructions from a separate, remote control device 1000, an example of which is shown in FIG. 1. A wireless receiver 24 is connected to the local processor 22 for receiving flow instructions from the remote control device 1000 and delivering the flow instructions to the local processor 22. The device 10 also includes a housing 26 containing the flow path assembly 16, the transcutaneous access tool 14, the reservoir 12, the dispenser 20, the local processor 22, and the wireless receiver 24.

As shown best in FIGS. 2a and 2b, the housing 26 of the fluid delivery device 10 is free of user input components for providing flow instructions to the local processor, such as electromechanical switches or buttons on an outer surface of the housing 26, or interfaces otherwise accessible to a user to adjust the programmed flow rate through the local processor. The lack of user input components allows the size, complexity and costs of the device 10 to be substantially reduced so that the device 10 lends itself to being small and disposable in nature. Examples of such devices are disclosed in co-pending U.S. patent application Ser. No. 09/943,992, filed on Aug. 31, 2001, and entitled DEVICES, SYSTEMS AND METHODS FOR PATIENT INFUSION, which is assigned to the assignee of the present application and has previously been incorporated herein by reference.

In order to program, adjust the programming of, or otherwise communicate user inputs to the local processor, the fluid delivery device 10 includes the wireless communication element, or receiver 24, as shown in FIG. 3, for receiving the user inputs from the separate, remote control device 1000 of FIG. 1. Signals can be sent via a communication element (not shown) of the remote control device 1000, which can include or be connected to an antenna 1300, shown in FIG. 1 as being external to the device 1000.

The remote control device 1000 has user input components, including an array of electromechanical switches, such as the membrane keypad 1200 shown. The remote control device 1000 also includes user output components, including a visual display, such as a liquid crystal display (LCD) 1100. Alternatively, the control device 1000 can be provided with a touch screen for both user input and output. Although not shown in FIG. 1, the remote control device 1000 has its own processor (hereinafter referred to as the "remote" processor) connected to the membrane keypad 1200 and the LCD 1100. The remote processor receives the user inputs from the membrane keypad 1200 and provides "flow" instructions for transmission to the fluid delivery device 10, and provides information to the LCD 1100. Since the remote control device 1000 also includes a visual display 1100, the fluid delivery device 10 can be void of an information screen, further reducing the size, complexity and costs of the device 10.

The communication element 24 of the device 10 preferably receives electronic communication from the remote control device 1000 using radio frequency or other wireless communication standards and protocols. In a preferred embodiment, the communication element 24 is a two-way communication element, including a receiver and a transmitter, for allowing the fluid delivery device 10 to send information back to the remote control device 1000. In such an embodiment, the remote control device 1000 also includes an integral communication element comprising a receiver and a transmitter, for allowing the remote control device 1000 to receive the information sent by the fluid delivery device 10.

The local processor 22 of the device 10 contains all the computer programs and electronic circuitry needed to allow a user to program the desired flow patterns and adjust the program as necessary. Such circuitry can include one or more microprocessors, digital and analog integrated circuits, resistors, capacitors, transistors and other semiconductors and other electronic components known to those skilled in the art. The local processor 22 also includes programming, electronic circuitry and memory to properly activate the dispenser 20 at the needed time intervals.

In the exemplary embodiment of FIG. 3, the device 10 also includes a power supply 28, such as a battery or capacitor, for supplying power to the local processor 22. The power supply is preferably integrated into the fluid delivery device 10, but can be provided as replaceable, e.g., a replaceable battery. The device 10 can also include sensors or transducers such as a flow condition sensor assembly 30 or dispenser position monitors 32, for transmitting information to the local processor 22 to indicate how and when to activate the dispenser 20, or to indicate other parameters determining fluid flow, as well as conditions such as the reservoir being empty or leaking, or the dispensing of too much or too little fluid from the reservoir 12, etc.

As shown in FIG. 2b, the device 10 can also be provided with an adhesive layer 34 on the outer surface of the housing 26 for securing the device 10 directly to the skin of a patient, as illustrated in FIG. 1. The adhesive layer 34 is provided on an external "bottom" surface of the housing 26. The adhesive layer 34 is also preferably provided in a continuous ring encircling an external exit port 36 of the housing 26 in order to provide a protective seal around the penetrated patient's skin to prevent the penetrated skin from becoming contaminated when a cannula 38 of the transcutaneous access tool 14 extends through the skin. It is preferable that the fill port 18 extend through the bottom surface of the housing 26 to discourage and prevent filling and refilling of the fluid delivery device 10 when the device 10 is attached to a patient's skin. The housing 26 can be made from flexible material, or can be provided with flexible hinged sections that allow the fluid delivery device 10 to flex during patient movement to prevent detachment and aid in patient comfort.

As shown in FIGS. 2b and 3, an outlet plug 40 is secured to the distal end of the cannula 38 of the transcutaneous access tool 14 prior to use of the device 10. The outlet plug 40 has an air removal filter that allows air but not fluid to exit the cannula 38, and acts as a flow restriction system that operates to substantially prime (i.e., purge of air) the flow path of the fluid delivery device 10 prior to operation of the device 10, to ensure that a desired volume of fluid is accurately delivered by the device 10 during operation.

In the exemplary embodiment of FIG. 3, the reservoir 12 is not pressurized, and the dispenser 20 is adapted to control flow from the reservoir 12 by driving or pumping the fluid from the reservoir to the transcutaneous access tool 14. Examples of such "driving or pumping" dispensers are shown in co-pending U.S. patent application Ser. No. 09/955,623, filed on Sep. 19, 2001, and entitled PLUNGER FOR PATIENT INFUSION DEVICE, which is assigned to the assignee of the present application and incorporated herein by reference. Other examples of dispensers are shown in co-pending U.S. patent application Ser. No. 10/128,205, filed on Apr. 23, 2002, and entitled DISPENSER FOR PATIENT INFUSION DEVICE, which is assigned to the assignee of the present application and incorporated herein by reference, and co-pending U.S. patent application Ser. No. 10/128,203, filed on Apr. 23, 2002, and entitled DISPENSER FOR PATIENT INFUSION DEVICE, which is assigned to the assignee of the present application and incorporated herein by reference. Further examples of dispensers are shown in co-pending U.S. patent application Ser. No. 10/163,688, filed on Jun. 9, 2002, and entitled PLUNGER FOR PATIENT INFUSION DEVICE, which is assigned to the assignee of the present application and incorporated herein by reference, and in co-pending U.S. patent application Ser. No. 10/163,690, filed on Jun. 9, 2002, and entitled PLUNGER FOR PATIENT INFUSION DEVICE, which is also assigned to the assignee of the present application and incorporated herein by reference.

Figure 4A:
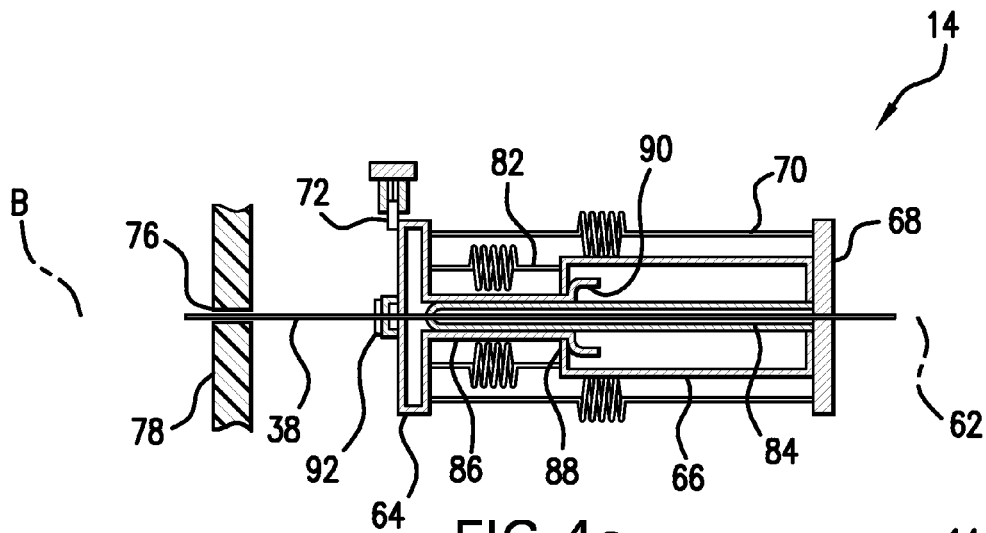
FIGS. 4a–4c are simplified schematic views of the transcutaneous access tool of the fluid delivery device of FIG. 3 illustrating deployment of a needle of the tool.
Figure 4B:
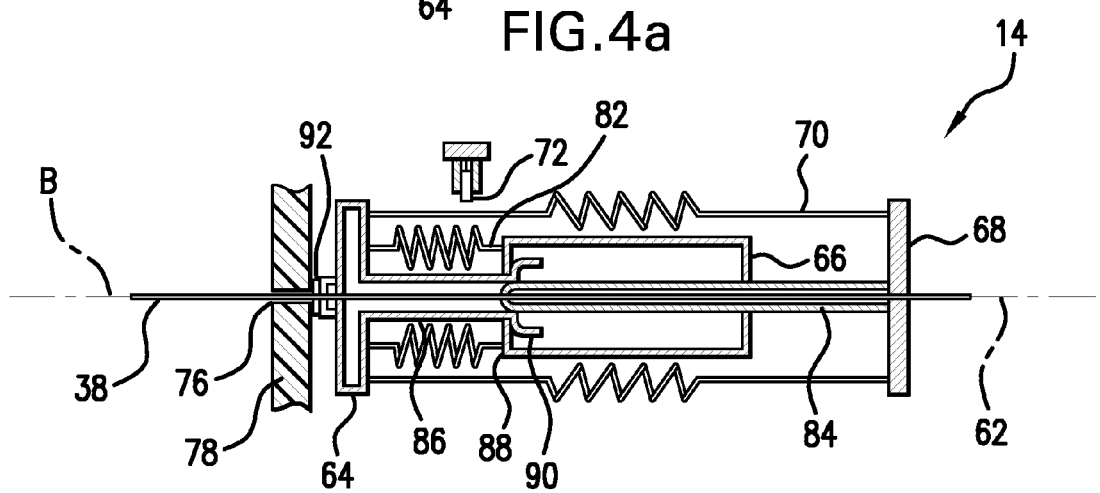
Figure 4C:
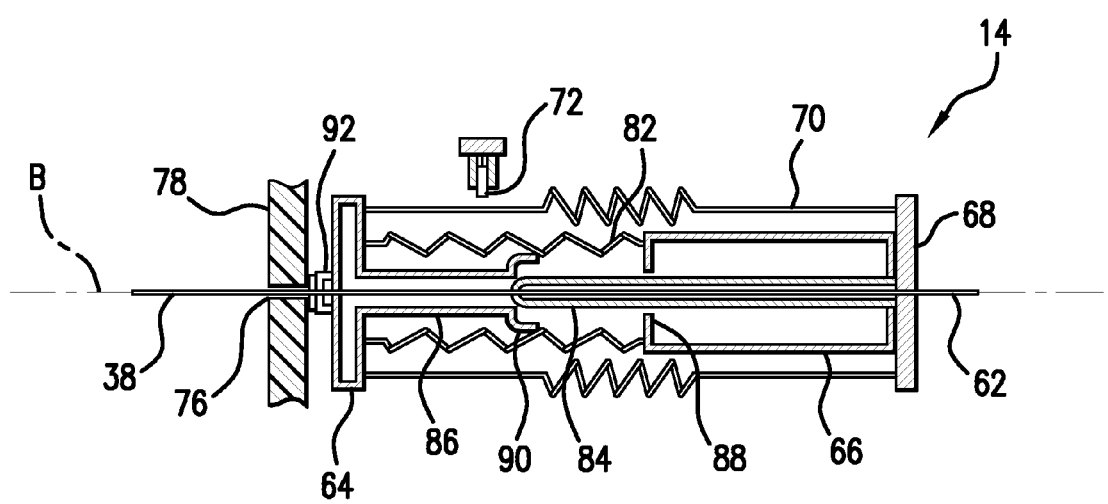
Figure 5:
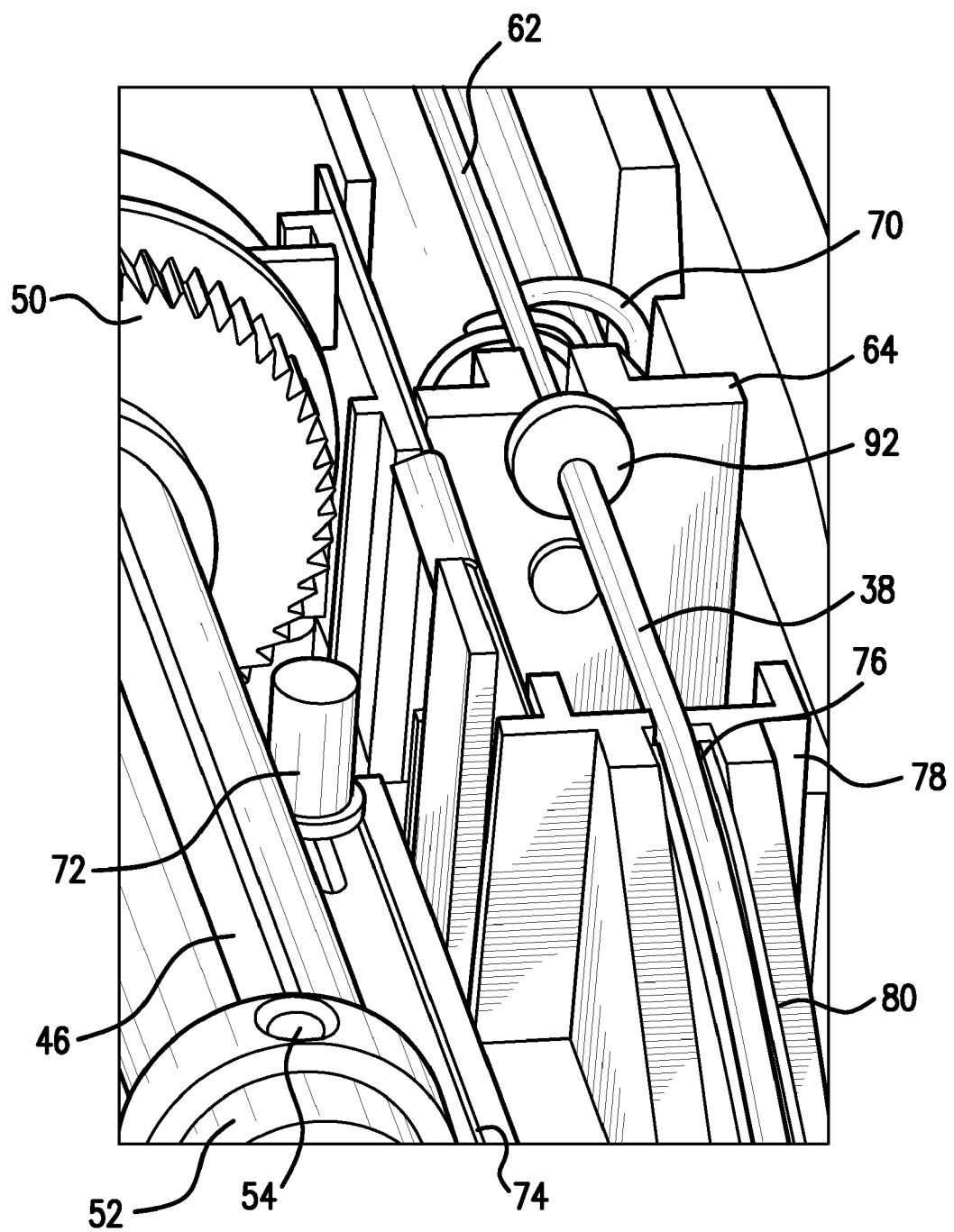
FIG. 5 is a further enlarged end perspective view of the transcutaneous access tool of FIG. 3 showing an exemplary embodiment of an exit port seal constructed in accordance with the present invention for sealing the exit port of the device housing upon deployment of the needle of the deployment of a needle of the tool.

In the embodiment shown in FIGS. 4 and 5, the reservoir 12 includes a cylindrical side wall 42 extending towards an outlet 44 connected to the transcutaneous access tool 14. A threaded lead screw 46 is received in the reservoir 12 and extends towards the outlet 44 of the reservoir 12 generally parallel with the side wall 42 of the reservoir 12, and a plunger 48 is secured to an end of the lead screw 46. The lead screw 46, the plunger 48 and the reservoir 12 are adapted (e.g., provided with o-rings) such that a fluid-tight seal is formed between the plunger 48 and the lead screw 46 and a fluid-tight seal is formed between the plunger 48 and the side wall of the reservoir 12, so that movement of the plunger 48 towards the outlet 44 of the reservoir 12 forces fluid through the outlet 44 to the transcutaneous access tool 14.

The dispenser 20 causes fluid flow by causing linear movement of the lead screw 46 and the plunger 48 towards the outlet 44 of the reservoir 12. Although not shown in FIG. 3, the dispenser 20 includes an elongated shape memory element connected to the local processor 22 and having a changeable length decreasing from an uncharged length to a charged length when at least one charge is applied to the shape memory element. The shape memory element is operatively connected to the plunger 48 such that the changeable length of the shape memory element causes the plunger 48 to move along the side wall 42 of the reservoir 12.

In the exemplary embodiment shown in FIG. 3, the dispenser 20 includes a rotatable gear 50 linearly fixed with respect to the reservoir 12. The gear 50 is coaxially fixed to an exterior surface of a slotted tube 52 such that rotation of the gear 50 causes rotation of the slotted tube 52 about a common longitudinal axis "A". The lead screw 46 is coaxially positioned within the slotted tube 52 and includes a radially extending pin 54 slidingly received in longitudinal slots of the slotted tube 52 such that rotation of the slotted tube 52 causes rotation of the lead screw 46. The lead screw 46 is also threadedly engaged with a fixed nut assembly 56, such that rotation of the gear 50 causes linear movement of the lead screw 46 through the fixed nut assembly 56 and linear movement of the plunger 48 towards the outlet 44 of the reservoir 12. In one exemplary embodiment, the fixed nut assembly 56 is configured to be disengaged from the lead screw 46 prior to use of the device to allow the lead screw 46 and the plunger 48 to be linearly moved away from an inlet 58 of the reservoir 12 during filling of the reservoir 12 through the fill port 18.

The dispenser 20 further includes a ratchet member 60 for engaging radially extending teeth of the gear 50, wherein the ratchet member 60 and the gear 50 are adapted such that linear movement of the ratchet member 60 in a first direction adjacent the gear 50 causes rotation of the gear 50, while linear movement of the ratchet member 60 in a second direction adjacent the gear 50 causes no rotation of the gear 50. The elongated shape memory element (not viewable) is connected to the ratchet member 60 such that the changeable length of the shape memory element decreasing from an uncharged length to a charged length causes linear movement of the ratchet member 60 in one of the first and the second directions. The dispenser 20 can also include a return element, such as a hinge spring (not viewable), connected to the ratchet member 60 for causing linear movement of the ratchet member 60 in the first direction.

It should be understood, however, that other types of dispensers can also be used with a device incorporating the reservoir 12, the transcutaneous access tool 14, or the laminated flow path assembly 16 of the present inventions. For example, the reservoir 12 can be pressurized and a dispenser that does not create a driving or pumping force, but rather acts as a metering device, allowing pulses of fluid to pass from the pressurized reservoir 12, through the dispenser, to the transcutaneous access tool 14. Examples of such "metering" dispensers are shown in co-pending U.S. patent application Ser. No. 09/977,434, filed Oct. 12, 2001, and entitled LAMINATED PATIENT INFUSION DEVICE, which is assigned to the assignee of the present application and incorporated herein by reference. In any event, in the exemplary embodiment shown the dispenser is controlled by the local processor 22, which includes electronic programming, controls, and circuitry to allow sophisticated fluid delivery programming and control of the dispenser.

Referring now to FIGS. 3 through 5, the exemplary embodiment of the transcutaneous access tool 14 constructed in accordance with the present invention includes the first cannula 38, which is preferably flexible, and a rigid second cannula 62 disposed within the lumen of the flexible first cannula 38. The transcutaneous access tool 14 also includes a movable deployment member 64 secured to the first cannula 38, a movable retraction member 66 secured to the second cannula 62, and a stationary fixed member 68 secured to the housing 26.

The transcutaneous access tool 14 further includes a latch 72 that normally maintains the deployment member 64 and the first cannula 38 in a pre-deployment position against the bias force of a compressed helical deployment spring 70. A shape memory element 74 activated upon the application of an electrical charge removes the latch 72 from the travel path of the deployment member 64, thereby allowing the deployment spring 70 to drive the deployment member 64 and the retraction member 66 away from the fixed member 68 and toward an internal exit port 76 of a wall 78 of the housing 26, and force the distal tips of both the first cannula 38 and the second cannula 62 through the external exit port 36 and into the skin of the patient. FIG. 4a shows the transcutaneous access tool 14 prior to deployment, while FIG. 4b shows the transcutaneous access tool 14 after deployment with the deployment member 64 and the retraction member 66 moved fully away from the fixed member 68 by the deployment spring 70.

The transcutaneous access tool 14 is in fluid communication with the reservoir 12 of the device 10 at all times before and after injection of the first cannula 38 into the skin of the patient. The housing 26 includes a cannula guide portion 80 which deflects the cannula (e.g., by approximately 40°) as the cannula 38 passes between the internal exit port 76 and the external exit port 36. However, the cannula 38 does not have a bent distal end (e.g., bent approximately 90°).

A compressed helical retraction spring 82 biases the retraction member 66 away from the deployment member 64. After the second cannula 62 has injected the distal tip of the first cannula 38 into the skin of the patient, the retraction spring 82 is allowed to force the retraction member 66 away from the deployment member 64 and towards the fixed member 68, and withdraw the second cannula 62 from the skin of the patient, as shown in FIG. 4c. The deployment member 64, however, maintains the first cannula 38 in the skin of the patient such that a relatively comfortable flow path is created between the reservoir 12 and the patient.

In the exemplary embodiment of FIGS. 3 through 5, the transcutaneous access tool 14 includes an elongated prong 84 extending from the fixed member 68 parallel with an axis "B" of the transcutaneous access tool 14, spaced-apart, resiliently flexible fingers 86 extending from the deployment member 64 parallel with the axis "B" and slidingly received on the prong 84 of the fixed member 68, and a catch 88 of the retraction member 66 extending laterally inwardly with respect to the axis "B". The catch 88 catches on laterally enlarged distal ends 90 of the fingers 86 of the deployment member 64, and prevents the retraction member 66 from being moved away from the deployment member 64 when the fingers 86 are laterally held apart by the prong 84 of the fixed member 68, as shown in FIGS. 4a and 4b.

The prong 84 and the fingers 86, however, are sized so that the fingers 86 slide off a distal end of the prong 84 when the deployment member 64 is fully deployed by the deployment spring 70, as shown in FIG. 4c. The force of the retraction spring 82 causes the catch 88 of the retraction member 66 to force the laterally enlarged distal ends 90 of the fingers 86 laterally together (i.e., squeeze the fingers 86 together) and be released from the laterally enlarged distal ends 90. The retraction spring 82 then forces the retraction member 66 away from the deployment member 64 and towards the fixed member 68, and withdraws the second cannula 62 from the skin of the patient, as shown in FIG. 4c.

Referring to FIGS. 3 through 5, the trancutaneous access tool 14 also includes an seal 92 that is moved between the deployment member 64 and the wall 78 of the housing 26 defining the internal exit port 76 upon deployment of the cannula 38. The seal 92 provides a substantially fluid-tight seal between the deployment member 64 and the wall 78 of the housing 26 when the deployment member 64 is moved against the wall 78, as shown in FIG. 4c. The seal 92 allows a fluid or gas, such as a sterilization medium (e.g., ethylene oxide), to enter the internal exit port 76 from outside the housing 26 prior to deployment of the cannula 38, but seals the housing 26 in a fluid-tight manner upon deployment of the cannula 38.

In the exemplary embodiment shown, the seal 92 is annular in shape, is coaxially positioned about the first cannula 38, and is secured to the deployment member 64. The seal 92 is made from a resiliently flexible material such as an elastomer or rubber. The seal 92 can also be bonded to an outer surface of the first cannula 38.

Figure 10:
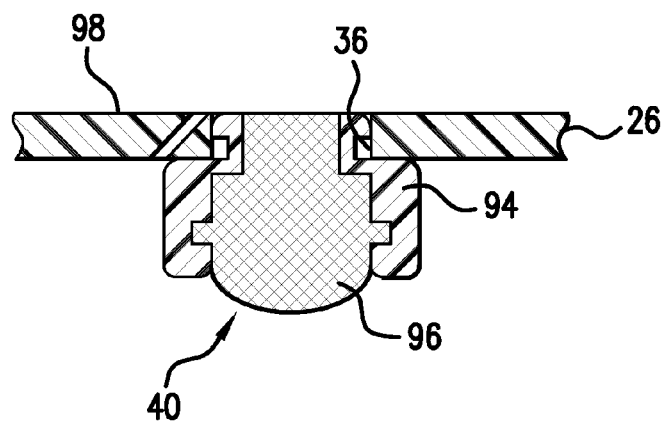
FIG. 10 is an enlarged sectional view of an exemplary embodiment of an outlet plug constructed in accordance with the present invention shown positioned within an outlet port of a housing a fluid delivery device, and wherein the housing includes a sterilization access port adjacent the outlet port.

Referring to FIG. 10, if the outlet plug 40, which includes a side collar portion 94 and a central air filter portion 96, is connected to the distal end of the cannula 38 prior to use of the fluid delivery device 10, the housing 26 can further be provided with a sterilization access port 98 adjacent the external exit port 36. As its name implies, the sterilization access port 98 allows a sterilization medium to enter the housing 26 when the outlet plug 40 is blocking the external exit port 36. Alternatively, the outlet plug 40 can be provided with its own sterilization access port, which would be formed in the side collar portion 94 of the outlet plug.

Figure 11:
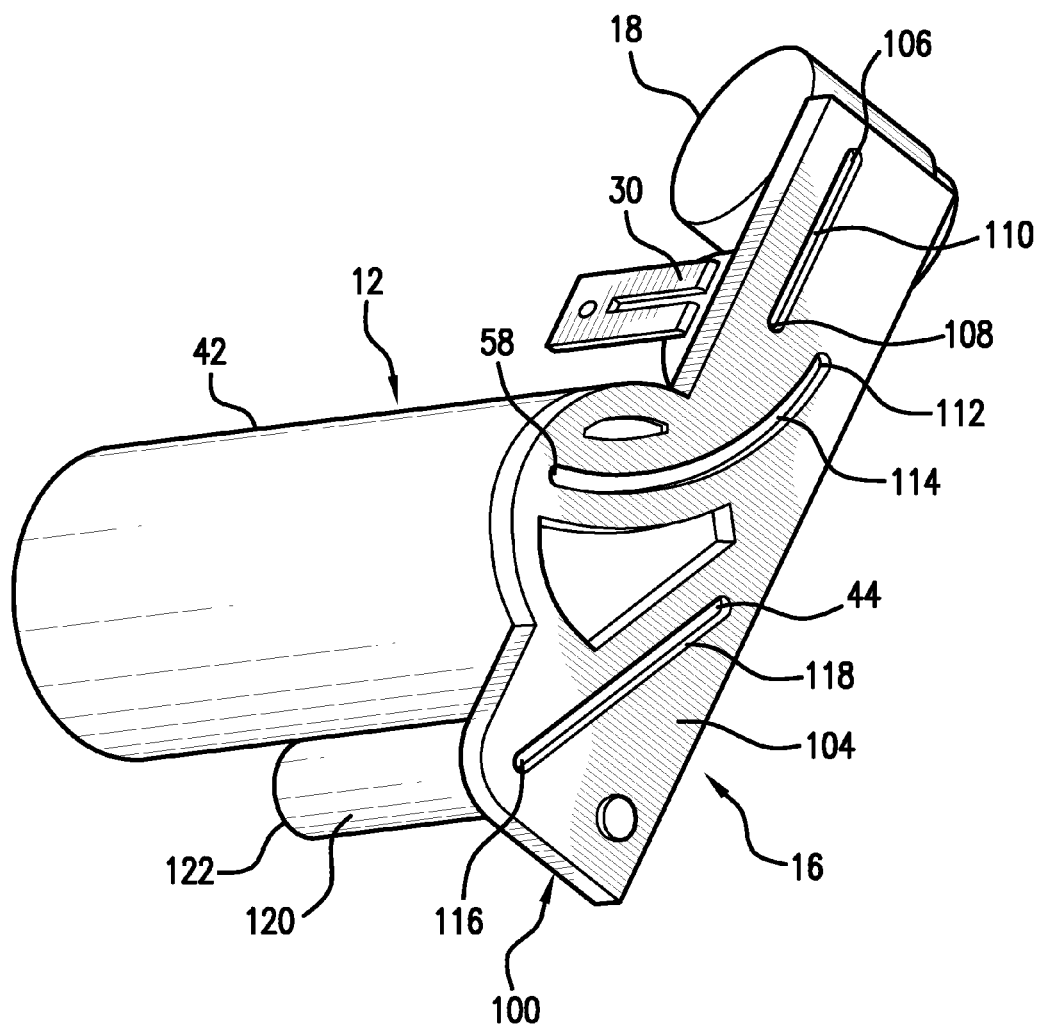
FIG. 11 is an enlarged end perspective view of a portion of the laminated flow path assembly of the fluid delivery device of FIG. 3.

Referring now to FIGS. 3 and 11, the exemplary embodiment of the flow path assembly 16 includes a base layer 100 having opposing first and second surfaces 102, 104. The base layer 100 defines a fill chamber outlet port 106 extending through the base layer 100 and between the opposing first and second surfaces 102, 104, an auxiliary chamber inlet port 108 extending through the base layer 100 and between the opposing first and second surfaces 102, 104, and a first groove 110 on the second surface 104 of the base layer 100 connecting the fill chamber outlet port 106 to the auxiliary chamber inlet port 108. The base layer 100 also defines an auxiliary chamber outlet port 112 extending through the base layer 100 and between the opposing first and second surfaces, the reservoir inlet port 58 extending through the base layer 100 and between the opposing first and second surfaces, and a second groove 114 on the second surface 104 of the base layer 100 connecting the auxiliary chamber outlet port 112 to the reservoir inlet port 58. The base layer 100 further defines the reservoir outlet port 44 extending through the base layer 100 and between the opposing first and second surfaces, a cannula inlet port 116 extending through the base layer 100 and between the opposing first and second surfaces, and a third groove 118 on the second surface 104 of the base layer 100 connecting the reservoir outlet port 44 to the cannula inlet port 116.

As shown in FIG. 3, the flow path assembly 16 also includes a cover layer 118 substantially covering the second surface 104 of the base layer 100 in a substantially fluid-tight manner, such that the grooves 110, 114, 118 in the second surface 104 of the base layer 100 are formed into fluid passageways. Preferably, the base layer 100 is relatively rigid and the cover layer 118 is relatively flexible. The base layer 100 is preferably comprised of a relatively rigid plastic that is formed through injection molding, for example, while the cover layer 118 is made from a relatively flexible fluid-tight plastic, such as an elastomer, rubber or thermoplastic. The base layer 100 and the cover layer 118 are secured together in a suitable manner through bonding or by using an adhesive, for example, in order to seal the grooves 110, 114, 118 of the base layer 100 in a fluid-tight manner. Among other benefits and features, the laminated construction of the flow path assembly 16 simplifies manufacturing (and thus the cost) of the resulting fluid delivery device 10.

Referring to FIGS. 3 and 11, the flow path assembly 16 also includes a cannula connector member 120 secured to the first surface 102 of the base layer 100 in a substantially fluid-tight manner and defining a cannula connector chamber (not viewable) in fluid communication with the cannula inlet port 116 of the base layer 100. The connector member 120 includes a needle septum 122 fitted in an opening of the connector chamber. The second cannula 62 of the transcutaneous access tool 14 extends through the needle septum 122 to provide fluid communication between the reservoir 12 and the first cannula 38. Preferably, the connector member 120 is unitarily formed as a single piece with the base layer 100, by injection molding for example.

Still referring to FIGS. 3 and 11, the flow path assembly 16 also includes the fill port 18 secured to the first surface 102 of the base layer 100 in a substantially fluid-tight manner and defining a fill port chamber (not viewable) in fluid communication with the fill chamber outlet port 106 of the base layer 100. The fill port 18 includes a needle septum 124 (as shown in FIG. 2b) fitted in an opening of the fill port chamber. Preferably, the fill port 18 is unitarily formed as a single piece with the base layer 100, by injection molding for example.

Although not viewable, the first surface 102 of the base layer 100 defines an auxiliary recess connecting the auxiliary chamber inlet port 108 and the auxiliary chamber outlet port 112. The flow sensor assembly 30 is secured to the auxiliary recess of the first surface 102 of the base layer 100 in a substantially fluid-tight manner, and the flow sensor assembly 30 has a flow sensor chamber (not viewable) in fluid communication with the auxiliary chamber inlet port 108 and the auxiliary chamber outlet port 112 of the base layer 100. The flow sensor assembly provides an indication of fluid pressure within the flow path assembly 16, so that conditions within the flow path assembly can be determined. Examples of flow sensor assemblies are shown in co-pending U.S. patent application Ser. No. 10/087,507, filed on Mar. 1, 2002, and entitled FLOW CONDITION SENSOR ASSEMBLY FOR PATIENT INFUSION DEVICE, which is assigned to the assignee of the present application and incorporated herein by reference.

While the exemplary embodiment of the flow path assembly 16 of FIGS. 3 and 11 includes the flow sensor assembly 30 in fluid communication with the auxiliary chamber inlet port 108 and the auxiliary chamber outlet port 112 of the base layer 100, the auxiliary chamber inlet port 108 and the auxiliary chamber outlet port 112 can be used to attach other types of "auxiliary" sensors or devices to the flow path assembly 16. For example, an auxiliary sensor connected to the auxiliary chamber inlet port 108 and the auxiliary chamber outlet port 112 can be provided to not only detect flow conditions but other parameters such as detection of air, temperature monitoring, drug parameter monitoring (concentration, pH, etc.) and other parameters important to infusion of liquid therapeutics, in addition to flow rate. An auxiliary device can include an air removal filter, a fluid sterilization filter, a pressure release valve, and other types of devices as desired.

Referring to FIG. 3, the first surface 102 of the base layer 100 defines a reservoir shelf 126 connecting the reservoir 58 inlet port and the reservoir outlet port 44. The reservoir 12 includes the cylindrical side wall 42 having opposing open ends, and one of the open ends is received in a fluid-tight manner on the shelf 126 of the base layer 100 so that a interior chamber of the reservoir 12 is in fluid communication with the reservoir inlet port 58 and the reservoir outlet port 44 of the base layer 100. The side wall 42 of the reservoir 12 can be made of any suitably strong and rigid material that is compatible with the fluid to be held by the reservoir 12 and that can be sterilized. In one exemplary embodiment, the side wall 42 is comprised of stainless steel (in FIG. 3 the side wall 42 is shown as being transparent only for purposes of illustration). It is also contemplated that the side wall 42 can be formed unitarily as a single piece with the base layer 100, if desired.

Referring now to FIGS. 6 through 9, another fluid delivery device 130 constructed in accordance with the present invention is shown. The fluid delivery device 130 includes a housing 132 having a port 134, an adhesive layer 136 provided on an exterior surface of the housing 132 surrounding the port 134 and including resiliently flexible flaps 138 normally sealing the port 134 in a substantially fluid-tight manner. The adhesive layer 136 is for securing the device 130 to a patient during use.

Figure 6:
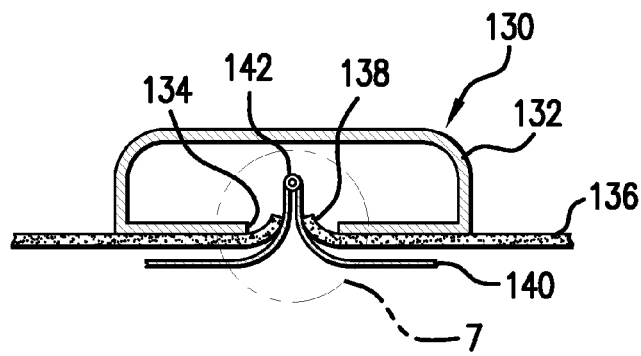
FIG. 6 is a sectional view of a fluid delivery device including an exemplary embodiment of a exit port seal assembly constructed in accordance with the present invention.
Figure 7:
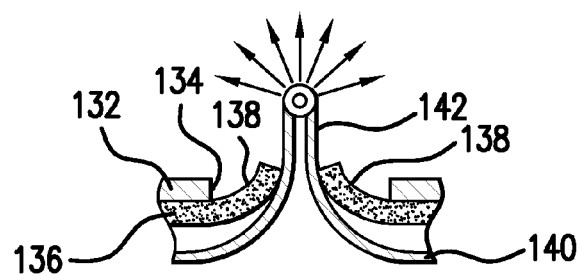
FIG. 7 is an enlarged sectional view of a portion of the exemplary embodiment of the exit port seal assembly contained in circle 7 of FIG. 6, illustrating how the assembly allows an interior of the device to be sterilized prior to use of the device.
Figure 8:
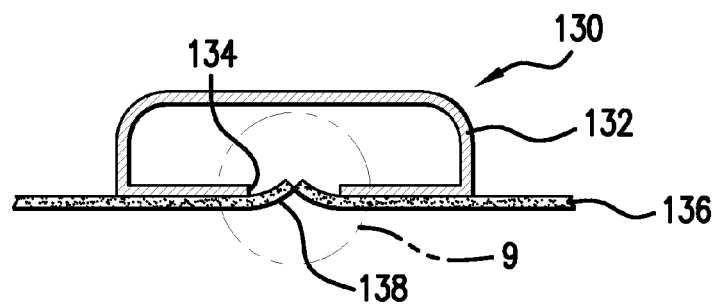
FIG. 8 is a sectional view of the fluid delivery device of FIG. 6 showing a protective bottom layer of the exit port seal assembly removed.
Figure 9:
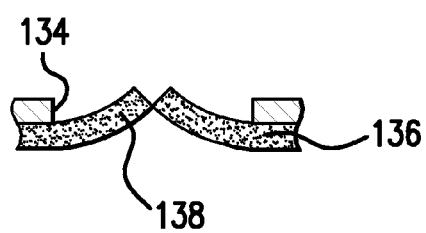
FIG. 9 is an enlarged sectional view of a portion of the exemplary embodiment of the exit port seal assembly contained in circle 9 of FIG. 8, illustrating how the assembly seals the interior of the device upon removal of the protective bottom layer and prior to use of the device.

A protective layer 140 removably covers the adhesive layer 136 and includes a sterilization access tube 142 extending through the flaps 138 of the adhesive layer 136 and into the housing 132. Among other benefits and features, the sterilization access tube 142 allows a fluid or gas, such as a sterilization medium (e.g., ethylene oxide), to enter the port 134 from outside the housing 132 prior to removal of the protective layer 140. The flaps 138 then seal the port 134 in a fluid-tight manner after removal of the protective layer 140, to reduce the risks of contamination of the fluid delivery device 130 during use. FIGS. 6 and 7 shown the device 130 prior to removal of the protective layer 140, while FIGS. 8 and 9 show the device 130 after removal of the protective layer 140. The port 134 may also be used for passage of a deployable cannula or other transcutaneous access tool (not shown), or may be provided just to allow access of a sterilization medium through the sterilization access tube 142 prior to use.

Figure 12:
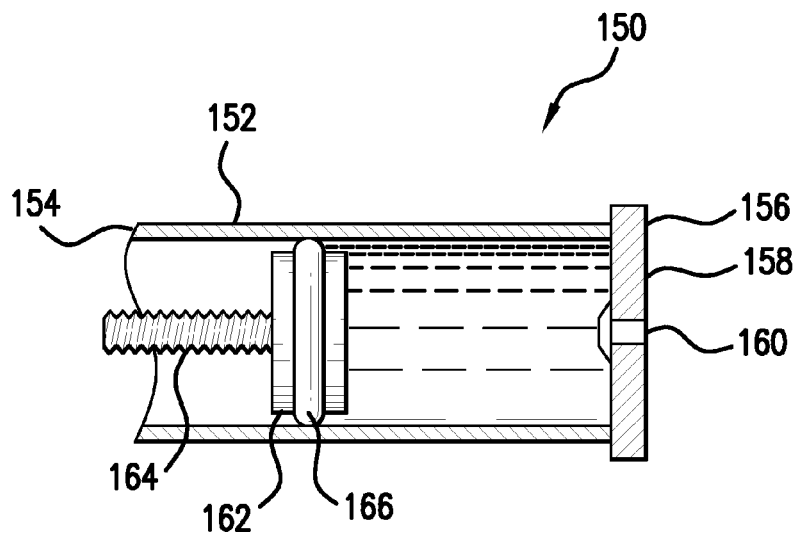
FIG. 12 is an enlarged sectional view of an exemplary embodiment of a fluid reservoir and a reservoir end wall constructed in accordance with the present invention, and an exemplary embodiment of a plunger and a lead screw constructed in accordance with the present invention and received in the reservoir for forcing fluid towards the end wall.

Referring to FIG. 12, another exemplary embodiment of a reservoir 150 constructed in accordance with the present invention is shown. The reservoir 150 includes a cylindrical side wall 152 having opposing first and second open ends 154, 156 and defining a reservoir chamber, an end cap 158 closing the second open end 156 of the side wall 152 and defining a port 160 providing fluid communication with the reservoir chamber, a plunger 162 received in the reservoir chamber and slidingly moveable along the side wall 152 and between the opposing first and second open ends 154, 156, and a lead screw 164 extending into the first open end 154 of the side wall 152 and having a distal end secured to the plunger 162.

Figure 13:
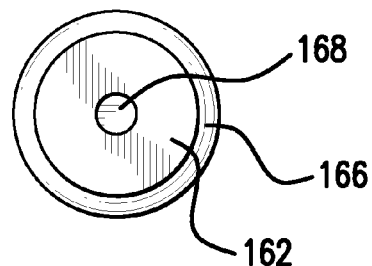
FIG. 13 is a first end view of the plunger of FIG. 12.

In the exemplary embodiment of FIGS. 12 and 13, a resiliently flexible o-ring 166 is provided in a circumferential groove of the plunger 162 to maintain a fluid-tight seal between the plunger 162 and the side wall 152 of the reservoir 150. The distal end of the lead screw 164 is preferably rotatably secured within a socket 168 of the plunger 162 so that the lead screw 164 can be rotated independently of the plunger 162. In addition, the distal end of the lead screw 164 is preferably snap-fit into the socket 168 for ease of assembly. The end cap 158 is made of a suitably rigid and strong material that is compliant with the fluid to be held in the reservoir 150 and that can be easily sterilized, such as stainless steel. The end cap 158 can be secured to the side wall 152 by welding for example.

Figure 14:
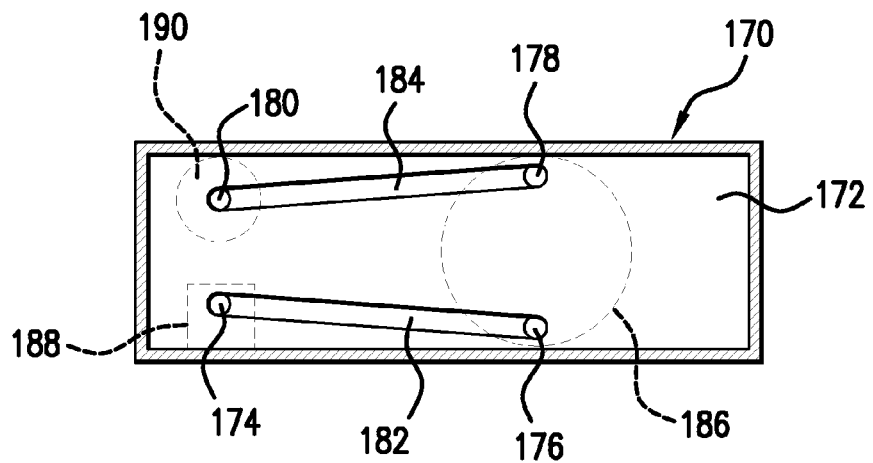
FIG. 14 is a second end view of a portion of an exemplary embodiment of a laminated flow path constructed in accordance with the present invention for attachment to the end wall of the reservoir of FIG. 12.

An exemplary embodiment of a flow path assembly constructed in accordance with the present invention includes the reservoir 150 of FIGS. 12 and 13 assembled to a base layer 170 of FIG. 14. The base layer 170 has opposing first and second surfaces 172 (only the second surface is viewable in FIG. 14), a fill chamber outlet port 174 extending through the base layer 170 and between the opposing first and second surfaces, a reservoir inlet port 176 extending through the base layer 170 and between the opposing first and second surfaces, a reservoir outlet port 178 extending through the base layer 170 and between the opposing first and second surfaces, and a cannula inlet port 180 extending through the base layer 170 and between the opposing first and second surfaces. The second surface 172 of the base layer 170 defines a first groove 182 connecting the fill chamber outlet port 174 to the reservoir inlet port 176, and a second groove 184 connecting the reservoir outlet port 178 to the cannula inlet port 180.

The first surface of the base layer 170 defines a reservoir recess 186 connecting the reservoir inlet port 176 and the reservoir outlet port 178 and for receiving the end cap 158 of the reservoir 150 of FIG. 12 in a substantially fluid-tight manner. The port 160 of the end cap 158 provides fluid communication between the reservoir 150 and the reservoir inlet port 176 and the reservoir outlet port 178. During assembly, the end cap 158 of the reservoir 150 is snap-fit into the reservoir recess 186 of the base layer 170.

Referring to FIG. 14, the first surface of the base layer 170 also defines a fill port recess 188 over the fill chamber outlet port 174 and a cannula connector recess 190 over the cannula inlet port 180. The base layer 170 is made of a suitable strong and rigid material, such as injection molded plastic or stainless steel. Although not shown, the flow path assembly further includes a cover layer secure over the second surface 172 of the base layer 170 in a fluid-tight manner such that the grooves 182, 184 are formed into fluid passageways. Among other benefits and features, the mating construction of the reservoir 150 and the base layer 170 of FIGS. 12 through 14 simplifies assembly (and thus the cost) of the resulting fluid delivery device.

Figure 15:
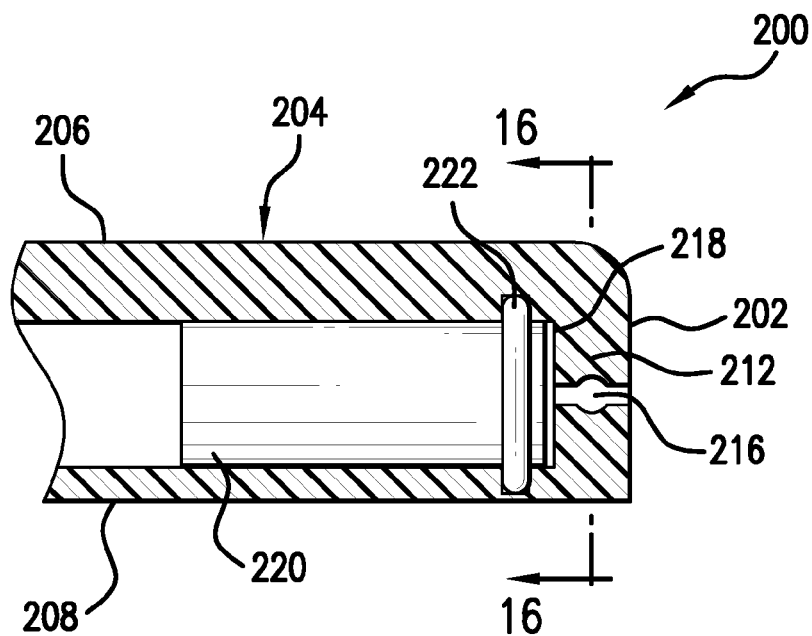
FIG. 15 is a sectional view of an exemplary embodiment of a fluid reservoir constructed in accordance with the present invention, and an exemplary embodiment of a device housing including a laminated flow path constructed in accordance with the present invention.
Figure 16:
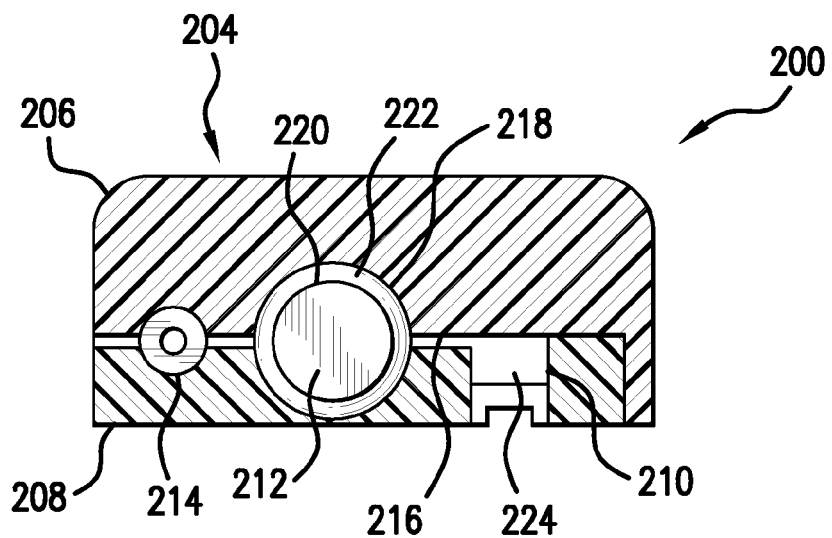
FIG. 16 is a sectional view taken along line 16—16 of FIG. 15 of the device housing showing the laminated flow path connected to the reservoir.

Referring to FIGS. 15 and 16, an additional flow path assembly 200 constructed in accordance with the present invention is shown. In general, the flow path assembly 200 of FIGS. 15 and 16 is unitarily formed as part of an end wall 202 of a housing 204 of a fluid delivery device. Among other benefits and features, the flow path assembly 200 of FIGS. 15 and 16 simplifies assembly (and thus the cost) of the fluid delivery device by incorporating the flow path into the end wall 202 of the housing 204, which can be two injection molded pieces 206, 208 assembly together.

In the exemplary embodiment shown, the flow path assembly 200 includes a first portion 206 and a second portion 208 of the housing 204 assembled together to form the end wall 202 of the housing. The end wall 202 includes a fill port 210, a reservoir connection port 212, a cannula connection port 214, and at least one flow path 216 connecting the fill port, the reservoir connection port and the cannula connection port.

In the exemplary embodiment shown, the first portion 206 of the housing 204 includes a first portion of the end wall 202 and the second portion 208 of the housing 204 includes a second portion of the end wall 202. The first and the second portions of the end wall 202 have mating surfaces defining corresponding grooves which together define the flow path 216 of the end wall when the first and the second portions 206, 208 of the housing 204 are assembled together.

The end wall 202 of the housing 204 further includes an interior surface defining a reservoir recess 218 in fluid communication with the reservoir connection port 212, and a reservoir side wall 220 is received in the recess 218. A circumferential o-ring groove is provided in the reservoir recess 218, and a resiliently flexible o-ring 222 is positioned in the groove to provide a fluid-tight seal between the side wall 220 of the reservoir and the end wall 202 of the housing 204. The fill port 210 extends between the mating surface of the second portion of the end wall 202 and an exterior surface of the second portion 208 of the housing 204, and contains a needle septum 224.

As illustrated by the above described exemplary embodiments, the present invention generally provides new and improved components for a device for delivering fluid, such as insulin for example, to a patient. It should be understood that the embodiments described herein are merely exemplary and that a person skilled in the art may make variations and modifications to the embodiments described without departing from the spirit and scope of the present invention. All such equivalent variations and modifications are intended to be included within the scope of this invention as defined by the appended claims.

What is claimed is:

1. A transcutaneous access tool comprising:
   a first cannula moveable along an axis of the transcutaneous access tool;
   a fixed member including an elongated prong extending parallel with the axis;
   a deployment member secured to the first cannula and movable along the axis away from the fixed member, the deployment member including spaced-apart, resiliently flexible fingers extending parallel with the axis and slidingly received on the prong of the fixed member, the fingers having distal ends that are laterally enlarged with respect to the axis;
   a second cannula disposed within the lumen of the first cannula;
   a retraction member secured to the second cannula and movable along the axis between the fixed member and the deployment member, wherein the retraction member includes at least one catch extending laterally inwardly with respect to the axis and catching on the laterally enlarged distal ends of the fingers of the deployment element when the fingers are laterally held apart by the prong of the fixed member; and
   a deployment spring biasing the deployment member away from the fixed member; and
   a retraction spring biasing the retraction member away from the deployment member and towards the fixed member.

2. A transcutaneous access tool according to claim 1, further comprising a deployment latch mechanism maintaining the deployment member against the bias force of the deployment spring.

3. A transcutaneous access tool according to claim 2, wherein the deployment latch mechanism comprises:
   a movable latch positioned in the path of the deployment member to maintain the deployment member against the bias force of the deployment spring; and
   an elongated shape memory element having a changeable length decreasing from an uncharged length to a charged length when at least one charge is applied to the shape memory element, the shape memory element connected to the latch such that the changeable length of the shape memory element decreasing from an uncharged length to a charged length causes the latch to be moved out of the path of the deployment member.

* * * * *